United States Patent
Stein

(10) Patent No.: US 10,939,951 B2
(45) Date of Patent: Mar. 9, 2021

(54) HIGH-FREQUENCY SURGICAL EQUIPMENT AND METHOD FOR OPERATING SUCH AN EQUIPMENT

(71) Applicant: OLYMPUS WINTER & IBE GMBH, Hamburg (DE)

(72) Inventor: Thomas Stein, Teltow (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 589 days.

(21) Appl. No.: 15/025,385

(22) PCT Filed: Nov. 14, 2014

(86) PCT No.: PCT/EP2014/074683
§ 371 (c)(1),
(2) Date: Mar. 28, 2016

(87) PCT Pub. No.: WO2015/074972
PCT Pub. Date: May 28, 2015

(65) Prior Publication Data
US 2016/0213416 A1    Jul. 28, 2016

(30) Foreign Application Priority Data
Nov. 19, 2013  (DE) .................. 10 2013 223 561.5

(51) Int. Cl.
*A61B 18/12*    (2006.01)
*A61B 18/00*    (2006.01)

(52) U.S. Cl.
CPC .. *A61B 18/1233* (2013.01); *A61B 2018/0063* (2013.01); *A61B 2018/00589* (2013.01);
(Continued)

(58) Field of Classification Search
CPC ...... A61B 18/1233; A61B 2018/00589; A61B 2018/00595; A61B 2018/1213; A61B 2018/0063; A61B 2018/1462
See application file for complete search history.

(56) References Cited

U.S. PATENT DOCUMENTS

| | | | |
|---|---|---|---|
| 4,114,623 | A | 9/1978 | Meinke et al. |
| 4,126,137 | A | 11/1978 | Archibald |

(Continued)

FOREIGN PATENT DOCUMENTS

| | | |
|---|---|---|
| CN | 1839768 A | 10/2006 |
| CN | 201759666 U | 3/2011 |

(Continued)

OTHER PUBLICATIONS

Jan. 9, 2018 Office Action issued in Japanese Patent Application No. 2016-532634.

(Continued)

*Primary Examiner* — Eun Hwa Kim
*Assistant Examiner* — Christine A Dedoulis
(74) *Attorney, Agent, or Firm* — Oliff PLC

(57) ABSTRACT

Disclosed is a high-frequency surgical appliance for cutting and/or coagulating biological tissue, having a high-frequency generator designed to produce a high-frequency alternating current during operation, and also a method for operating a high-frequency surgical appliance that involves a high-frequency alternating current produced by means of a high-frequency generator for of cutting and/or coagulating biological tissue. The high-frequency surgical appliance according to the invention has a power setting device that is arranged and designed to set or limit an output power of the high-frequency surgical appliance to a power value selected by a user. In addition, the high-frequency surgical appliance according to the invention has a spark control device that is (Continued)

Figure 1:
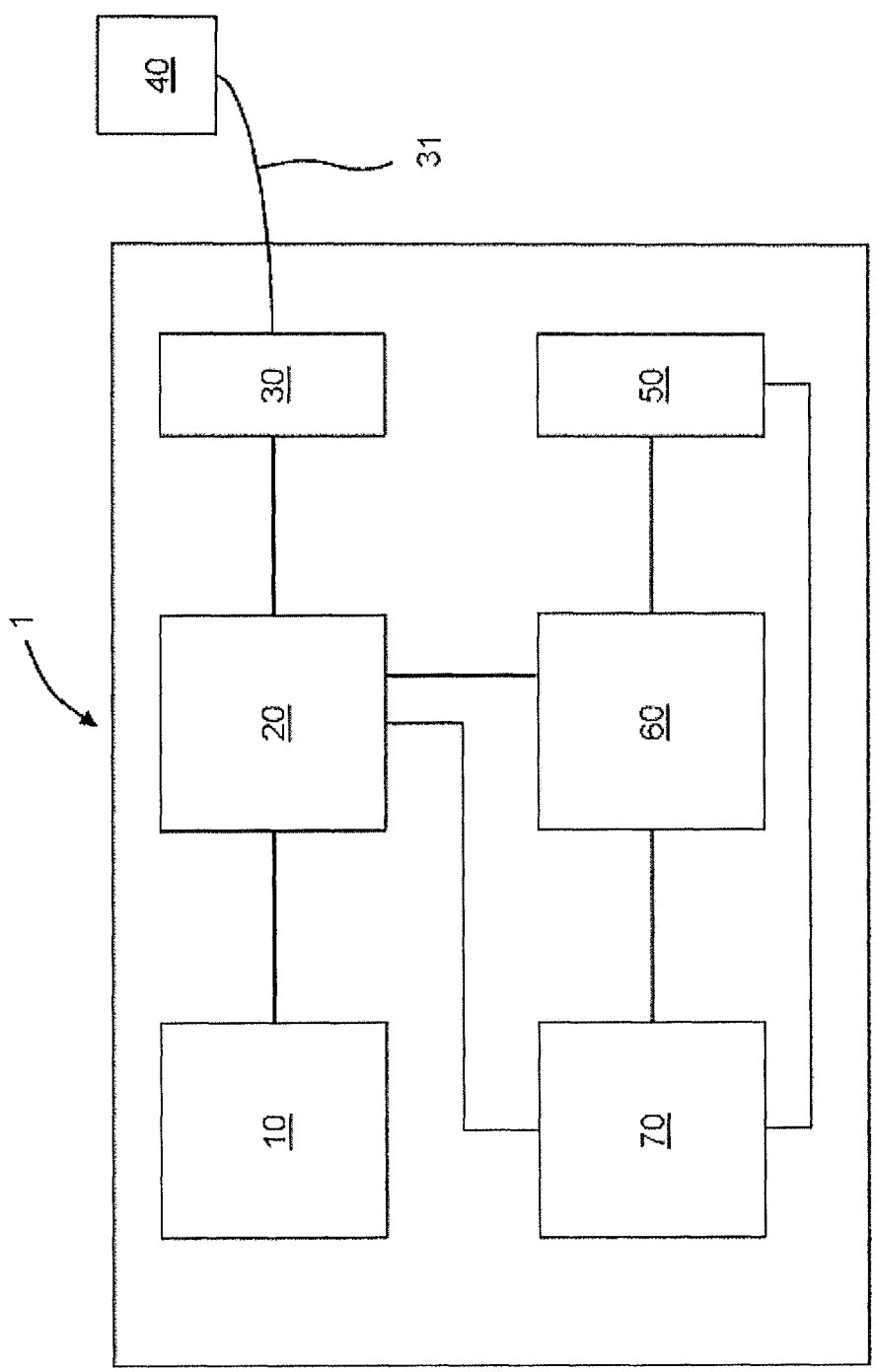

arranged and designed to set or limit a spark voltage to a setpoint spark value, the spark control device also being designed to ascertain the setpoint spark value on the basis of the power value selected by a user.

6 Claims, 2 Drawing Sheets

(52) U.S. Cl.
CPC .............. *A61B 2018/00595* (2013.01); *A61B 2018/00601* (2013.01); *A61B 2018/00607* (2013.01); *A61B 2018/00672* (2013.01); *A61B 2018/00678* (2013.01); *A61B 2018/00684* (2013.01); *A61B 2018/00702* (2013.01); *A61B 2018/00767* (2013.01)

(56) References Cited

U.S. PATENT DOCUMENTS

| | | | |
|---|---|---|---|
| 4,209,018 A | | 6/1980 | Meinke et al. |
| 5,108,391 A | * | 4/1992 | Flachenecker ..... A61B 18/1206 606/38 |
| 5,540,683 A | | 7/1996 | Ichikawa et al. |
| 5,599,344 A | | 2/1997 | Paterson |
| 5,628,745 A | | 5/1997 | Bek |
| 5,749,869 A | | 5/1998 | Lindenmeier et al. |
| 6,008,464 A | * | 12/1999 | Donnart ................... H05H 1/36 219/121.48 |
| 7,821,143 B2 | | 10/2010 | Wiener |
| 2004/0030329 A1 | * | 2/2004 | Hagg ................. A61B 18/1206 606/38 |
| 2013/0267947 A1 | * | 10/2013 | Orszulak ............ A61B 18/1233 606/41 |

FOREIGN PATENT DOCUMENTS

| | | | |
|---|---|---|---|
| DE | 25 04 280 B2 | 11/1976 | |
| DE | 41 26 608 A1 | 2/1993 | |
| DE | 42 17 999 A1 | 12/1993 | |
| DE | 4217999 A1 * | 12/1993 | ......... A61B 18/1206 |
| EP | 0 219 568 A1 | 4/1987 | |
| EP | 0 316 469 A1 | 5/1989 | |
| EP | 1157667 A2 | 11/2001 | |
| JP | S53-96292 A | 8/1978 | |
| JP | H07-124101 A | 5/1995 | |
| JP | 2002-078718 A | 3/2002 | |
| JP | 2003-235866 A | 8/2003 | |

OTHER PUBLICATIONS

Jan. 8, 2015 Search Report issued in International Patent Application No. PCT/EP2014/074683.
Jul. 13, 2017 Office Action issued in Chinese Patent Application No. 201480054284.0.
Nov. 8, 2019 Office Action issued in Japanese Patent Application No. 2016-532634.
Exhibit BM1_KLS Martin_Martin ME 402 Maximum Service-Handbuch, Exhibit from Summons with Preliminary Dpinion of the Opposition Division dated Jul. 25, 2019.
Exhibit BM2_Overview delivery 80613263, Exhibit from Summons with Preliminary Opinion of the Opposition Division dated Jul. 25, 2019.
Exhibit BM3a_Diagr. ME 402, Exhibit from Summons with Preliminary Opinion of the Opposition Division dated Jul. 25, 2019.
Exhibit BM3b_Diag. ME 402, Exhibit from Summons with Preliminary Opinion of the Opposition Division dated Jul. 25, 2019.
Exhibit BM4_email, Exhibit from Summons with Preliminary Opinion of the Opposition Division dated Jul. 25, 2019.
Exhibit Anlage BM5a example ME402, Exhibit from Submission of Opponent in EPO Proceedings dated Jan. 10, 2020.
Exhibit Anlage BM5b graphic, Exhibit from Submission of Opponent in EPO Proceedings dated Jan. 10, 2020.
Jul. 25, 2019 Summons with Preliminary Opinion of the Opposition Division.
Jan. 10, 2020 Submission Proprietor.
Dec. 21, 2018 Reply to Grounds of Opposition.
Excerpt Grounds of Opposition in reply to Submission Proprietor dated Jan. 10, 2020 (English Translation).
Excerpt Submission filed by Opponent in EPO Proceeding in reply to Submission of Proprietor dated Jan. 10, 2020 (English Translation).
Exhibit BM1b_KLS Martin_Martin ME 402 Maximum Service-Handbuch, Exhibit from Summons with Preliminary opinion of the Opposition Division dated Jul. 25, 2019.

* cited by examiner

HIGH-FREQUENCY SURGICAL EQUIPMENT AND METHOD FOR OPERATING SUCH AN EQUIPMENT

The invention relates to a high-frequency surgical equipment for cutting and/or coagulating biological tissue with a high-frequency generator which is designed to generate a high-frequency alternating current during operation.

The invention also relates to a method for operating a high-frequency surgical equipment in which a high-frequency alternating current is generated by means of a high-frequency generator for cutting and/or coagulating biological tissue.

The term high-frequency surgery is understood as meaning essentially the cutting and/or coagulating (sclerozing) of biological tissue by using high-frequency alternating current (preferably about 0.2 MHz or 0.3 MHz to 3 MHz, in some cases up to 5 MHz). For this purpose, high-frequency surgical systems with a high-frequency surgical equipment and an electrosurgical instrument connected thereto are preferably used.

In the case of coagulation, high-frequency alternating current is used in particular for stopping bleeding or for the ablation of tissue. This involves heating tissue surrounding an electrode of an electrosurgical instrument to the extent that denaturation and shrinkage of the tissue and the blood vessels occurs, and consequently ultimately the stopping of any bleeding. Also in the case of ablation, a region of tissue is denatured in this way. The region of tissue thus treated scars and is eliminated by the body's own processes, without having to be surgically removed.

In the cutting operation, the cutting effect in the biological tissue is based on the forming of an arc between an active electrode, known as the cutting electrode, of an electrosurgical instrument and the tissue. Electrically conductive tissue can in this case be severed almost without any mechanical pressure.

In the case of the monopolar technique, an active coagulating or cutting electrode of an electrosurgical instrument and a neutral electrode applied over a large surface area are used. The high-frequency current in this case flows from the active electrode via the tissue to be treated to the neutral electrode. An active electrode of a small area in comparison with a neutral electrode of a large area is decisive for the thermal effect of the current at the application site. As a result, a high current density, and consequently a strong heating of the tissue, are achieved at the operating site, and at the same time unwanted instances of tissue damage on the neutral electrode are avoided.

In the case of bipolar applications, two electrodes are used, combined in an electrosurgical instrument or formed on different electrosurgical equipment. The high-frequency current in this case flows from the one electrode via the tissue to be treated to the other electrode of the electrosurgical instrument.

High-frequency surgical equipment of the type mentioned at the beginning are known from the prior art and serve the purpose of supplying electrosurgical instruments with high-frequency current. They are used in surgery for various procedures and treatments. For the different application areas, and for example on account of the tissue-dependent significantly different impedances of the tissue, high-frequency surgical equipment can be operated with a differing output power. At the same time, in the case of a lot of high-frequency surgical equipment, the spark intensity is limited and kept constant by means of what is known as spark control. The aim is to carry out treatments safely and efficiently for the patient and the user and in particular to achieve reproducible cutting and/or coagulating effects. One requirement for high-frequency surgical equipment is therefore to ensure reproducible cutting and/or coagulating properties, largely independently of external conditions, such as for example the cutting speed or electrode size. When electrosurgical systems are used, however, it may happen in practice that electrodes stick to the tissue or the cutting and/or coagulating quality is insufficient. This may lead to undesired interruptions in the treatment and/or prolong the treatment time.

Therefore, an object of the present invention is to provide a high-frequency surgical equipment and a method for operating such a high-frequency surgical equipment that improve existing high-frequency surgical equipment and associated operating methods. In particular, an object of the present invention is to provide a high-frequency surgical equipment and a corresponding operating method that can reduce the number and/or duration of interruptions in the treatment, and consequently preferably also reduce the treatment time.

This object is achieved according to the invention by a high-frequency surgical equipment for cutting and/or coagulating biological tissue with a high-frequency generator which is designed to generate a high-frequency alternating current during operation. The high-frequency surgical equipment also has a power setting device, which is arranged and designed to set or limit an output power of the high-frequency surgical equipment to a power value selected by a user. Also provided is a spark control device, which is arranged and designed to set or limit a spark voltage to a setpoint spark value, the spark control device also being designed to determine the setpoint spark value in dependence on the power value selected by a user.

High-frequency surgical equipment for cutting and/or coagulating biological tissue have a high-frequency generator which generates high-frequency alternating current. A power setting device allows the output power of the high-frequency surgical equipment to be selected by a user. For this purpose, the power setting device is preferably connected to a user interface, via which the user can select and stipulate the desired power value, for example by way of a for the controllers. The power setting device is preferably connected in signaling terms to the high-frequency generator in such a way that the power value selected by the user can be set.

A spark control device also provides a spark control of the high-frequency surgical equipment, in that the spark intensity is controlled by way of a limitation of the spark voltage to a setpoint spark value.

In the case of the high-frequency surgical equipment known in the prior art with a spark control that keeps the spark intensity constant independently of the power setting, it may happen, in particular with low spark intensities, that—although a spark is present—electrodes stick to the tissue, in particular relatively large, for example spatula-shaped electrodes, or the cutting quality in the case of a cutting electrode deteriorates. A common user reaction in such cases, that of using the power setting to increase the power, in most cases does not however have a positive influence on the disadvantages mentioned, since the spark control continues to limit the high-frequency generator to the preset constant spark intensity. Also irrespective of the disadvantages mentioned by way of example, in certain application cases it may be useful to be able to vary the spark intensity even for a spark-controlled high-frequency surgical equipment.

The invention is based here on the finding of providing a high-frequency surgical equipment in which a setpoint spark value to which the spark voltage is limited is determined in a spark control device in dependence on the power value chosen by the user. For this purpose, which setpoint spark values are to be used for various power values selected by a user to limit the spark voltage by the spark control device may be stored in the control device (or for example in a computing and/or storing unit connected to it). The setpoint spark values may for example be stored in the form of a characteristic curve that represents the setpoint spark value in dependence on the power value selected by the user.

By coupling the setpoint spark value to which the spark voltage is limited to the power setting that is selected by the user, and consequently can be influenced or varied by the user, it is possible to achieve the effect that on the one hand spark control is retained, and consequently the spark intensity is controlled, but at the same time the user is given the possibility of also influencing the spark intensity indirectly by varying the power value. The setting of the output power to the power value and the spark control for limiting the spark voltage to the setpoint spark value in this case preferably remain independent of one another, and are merely coupled by the spark control device determining the setpoint spark value in dependence on the power value.

A preferred refinement of the high-frequency surgical equipment is obtained by the spark control device being arranged and designed to determine the setpoint spark value in such a way that, at least in a certain range of values, the setpoint spark value increases as the power value increases. Here it is provided that a higher power value, selected by the user, is also assigned a higher setpoint spark value, and a correspondingly lower power value, selected by the user, is also assigned a lower setpoint spark value, or a correspondingly lower setpoint spark value is determined by the spark control device. In this way, the intuitive user expectation that, as the power value increases, the spark intensity also increases, can be replicated in the spark control device, making it particularly easy for the user to operate.

This coupling of an increasing setpoint spark value to an increasing power value is preferably provided at least in a certain range of values. This coupling may, however, also be formed over the entire output power range of the high-frequency surgical equipment. Alternatively, different couplings of the setpoint spark value to the power value may be provided in different ranges of values of the overall spectrum of the output power of the high-frequency surgical equipment. For example, it may be provided in one specific range of values, preferably at the lower end of the spectrum of the output power of the high-frequency surgical equipment, that even as the power value increases the setpoint spark value remains constant, and only increases as the power value increases in a range of values of a higher output power.

In a further refinement of the high-frequency surgical equipment, it is preferred that the spark control device is arranged and designed to determine the respective setpoint spark value in such a way that, at least in a certain range of values, the setpoint spark value increases in proportion to the power value.

A proportional coupling of the setpoint spark value to the power value has the advantage of a predictable and uniform increase in the spark intensity with the power value. Here, too, such a coupling is possible over the entire spectrum of the possible output power of the high-frequency surgical equipment or in one or more certain ranges of values within this overall spectrum.

It may also be provided that the spark control device is arranged and designed to determine the setpoint spark value in such a way that the setpoint spark value does not undershoot a predetermined minimum spark value and/or does not overshoot a predetermined maximum spark value.

A restriction of the spark value to a maximum value may be preferred for safety reasons. A restriction of the setpoint spark value to a minimum value may be preferred if for example the setting of spark values below the minimum spark value proves to be difficult or unreliable. This may be the case in particular with setpoint spark values of less than 5 V, so that a minimum spark value of for example 5 V is preferred.

High-frequency surgical equipment may have two, three or more operating modes. Such operating modes may differ in the setting of various parameters and preferably serve the purpose of providing parameter settings that for example support different cutting speeds. In such an operating mode, furthermore, one, two, three or more effect modes may be provided or be selectable by users.

It is particularly preferred if the spark control device is arranged and designed to determine the setpoint spark value in dependence on the respective operating mode and/or in dependence on the respective effect mode. In particular, different characteristic curves may be provided for the setpoint spark value in dependence on the various operating or effect modes.

Also preferred is high-frequency surgical equipment in which the power setting device is arranged and designed to limit the power value such that the power value does not undershoot a predetermined minimum power value and/or does not overshoot a predetermined maximum power value. The limitation of the output power to a range between a minimum power value and a maximum power value may in particular serve the purpose of limiting the output power to a range that is required for the application area and at the same time is safe both for the patient and for the user.

The determination of the setpoint spark value by the spark control device may in this case preferably take place by a minimum power value being assigned a specific setpoint spark value. From this setpoint spark value assigned to the minimum power value, an increase, for example a proportional increase, in the setpoint spark value can then advantageously take place with the increase in the power value.

According to a further aspect of the invention, the object mentioned at the beginning is achieved by a method for operating a high-frequency surgical equipment, in particular a high-frequency surgical equipment described above, in which a high-frequency alternating current is generated by means of a high-frequency generator for cutting and/or coagulating biological tissue, an output power of the high-frequency surgical equipment being set by means of a power setting device to a power value selected by a user and a setpoint spark value of a spark voltage being determined by means of a spark control device in dependence on the power value selected by a user, and the spark voltage also being limited to the setpoint spark value by means of the spark control device.

The method according to the invention serves in particular for operating a high-frequency surgical equipment as described above. For the advantages, implementing variants and implementing details of this method and its possible developments, reference is made to the foregoing description concerning the corresponding device features.

Figure 2:
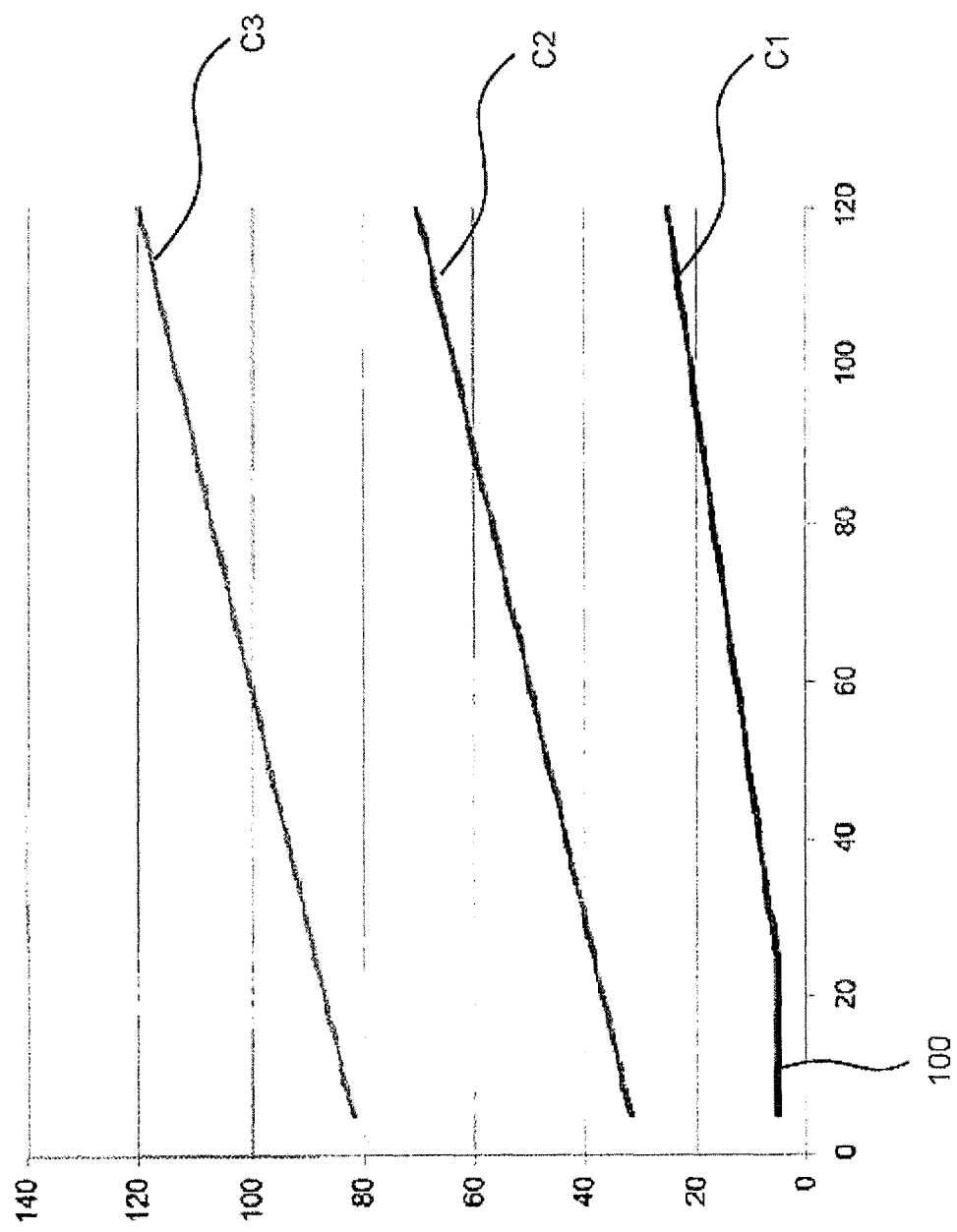

A preferred embodiment of the invention is described by way of example on the basis of the accompanying figures, in which:

FIG. 1 shows a schematic representation of an embodiment given by way of example of a high-frequency surgical equipment according to the invention; and FIG. 2 shows characteristic curves given by way of example of the setpoint spark value for a high-frequency surgical equipment as shown in FIG. 1.

FIG. 1 shows a high-frequency surgical equipment 1 for cutting and/or coagulating biological tissue with a high-frequency generator 20. The high-frequency generator 20 is connected to a power supply unit 10 and designed to generate a high-frequency alternating current during operation and deliver it via a connection socket 30 to an electrosurgical instrument 40 connected thereto by way of a connecting cable 31. A power setting device 60 is used for setting the output power of the high-frequency surgical equipment 1. Via a user interface 50, a user can select a desired power value and also an operating and/or effect mode, which is transmitted from the user interface 50 to the power setting device 60 and/or to the spark control unit 70. In dependence on this selected power value or operating and/or effect mode, the spark control unit 70 controls or limits the spark intensity of the high-frequency surgical equipment 1. The power setting device 60 and the spark control unit 70 are connected to one another and in each case to the high-frequency generator 20 and the user interface 50.

Stored in the high-frequency surgical equipment 1, preferably in the spark control unit 70, is how the setpoint spark value is determined in dependence on the power value chosen by the user. Assignments in the form of characteristic curves, as represented in FIG. 2, may be used for this purpose. On the vertical axis in FIG. 2, the spark voltage is plotted in volts; on the longitudinal axis, the chosen power stage of the high-frequency surgical equipment is plotted in watts. The three characteristic curves C1, C2 and C3 stipulate setpoint spark values for three different operating modes, here cutting modes, of the high-frequency surgical equipment 1. The characteristic curves C2 and C3 extend in a proportionally increasing manner in the range of values from a minimum power value of 5 W to a maximum power value of 120 W. The characteristic curve C1 exhibits a proportional coupling with the power value only in the range of values of 25 W to 120 W of the output power. In the range of values from 5 W to 25 W, the characteristic curve C1 has a non-proportional portion 100, in which the setpoint spark value is constantly at 5 V. The background for this is that, in particular in a range below 5 V, a precise setting of the spark voltage may be difficult.

By storing certain couplings, for example in the form of characteristic curves, of the setpoint spark values for certain power values, a user can consequently be given the possibility in an easy way of using a variation of the power value to bring about at the same time a variation of the spark intensity, without having to forego the advantages of spark control.

DESIGNATIONS

1 High-frequency surgical equipment
10 Power supply unit
20 High-frequency generator
30 Connection socket
31 Connecting cable
40 Electrosurgical instrument
50 User interface
60 Power setting device
70 Spark control device
100 Non-proportional range of spark values
C1, C2, C3 Operating modes

The invention claimed is:

1. A high-frequency surgical equipment for cutting or coagulating biological tissue, comprising:
a high-frequency generator configured to generate a high-frequency alternating current during operation;
a power setting device configured to set or limit an output power of the high-frequency surgical equipment to a power value selected by a user; and
a spark control device configured to set or limit a spark voltage to a setpoint spark value, and determine the setpoint spark value according to the power value selected by the user based on a stored curve relationship between power and setpoint spark in which for a range of values, the setpoint spark value increases as the power value increases,
wherein the high-frequency surgical equipment has more than one operating mode, and the spark control device is configured to determine the setpoint spark value according to a present operating mode, and
at least one of the operating modes has more than one effect mode, and the spark control device is configured to determine the setpoint spark value according to a present effect mode.

2. The high-frequency surgical equipment as claimed in claim 1, wherein the spark control device is configured to determine the setpoint spark value such that, within the range of values, the setpoint spark value increases in proportion to the power value.

3. The high-frequency surgical equipment as claimed in claim 1, wherein the spark control device is configured to determine the setpoint spark value such that the setpoint spark value does not undershoot a predetermined minimum spark value or does not overshoot a predetermined maximum spark value.

4. The high-frequency surgical equipment as claimed in claim 1, wherein the power setting device is configured to limit the power value such that the power value does not undershoot a predetermined minimum power value or does not overshoot a predetermined maximum power value.

5. The high-frequency surgical equipment as claimed in claim 1, wherein the spark control device is configured to determine the setpoint spark value such that a minimum power value is assigned a specific setpoint spark value.

6. A method for operating the high-frequency surgical equipment as claimed in claim 1, in which the high-frequency alternating current is generated by the high-frequency generator for cutting or coagulating biological tissue, comprising:
using the power setting device, setting the output power of the high-frequency surgical equipment to the power value selected by the user;
using the spark control device, determining the setpoint spark value according to the power value selected by the user based on the stored curve relationship between power and setpoint spark in which for the range of values, the setpoint spark value increases as the power value increases; and
using the spark control device, setting or limiting the spark voltage to the setpoint spark value.

* * * * *